US00PP31698P2

(12) United States Plant Patent
Mowrey et al.

(10) Patent No.: US PP31,698 P2
(45) Date of Patent: Apr. 28, 2020

(54) BLUEBERRY PLANT VARIETY NAMED 'DRISBLUENINETEEN'

(50) Latin Name: ***Vaccinium corymbosum* L.**
Varietal Denomination: DrisBlueNineteen

(71) Applicant: Driscoll's, Inc., Watsonville, CA (US)

(72) Inventors: Bruce D. Mowrey, Watsonville, CA (US); Esther Kibbe, Watsonville, CA (US); Marta C. Baptista, Watsonville, CA (US); Arturo Garcia, Watsonville, CA (US); Jennifer K. Izzo, Watsonville, CA (US); Brian K. Caster, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/350,226

(22) Filed: Oct. 16, 2018

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC ... A01H 5/08; A01H 5/00; A01H 5/02; A01H 4/00; A01H 6/36; A01H 6/368
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Caster et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Caster et al. |
| PP26,537 | P3 | 3/2016 | Caster et al. |
| PP26,643 | P3 | 4/2016 | Caster et al. |
| PP26,748 | P3 | 5/2016 | Caster et al. |
| PP27,622 | P3 | 1/2017 | Caster et al. |
| PP28,933 | P2 | 2/2018 | Caster et al. |

OTHER PUBLICATIONS

Caster et al., U.S. Appl. No. 16/350,012, filed Sep. 12, 2018, titled "Blueberry Plant Variety Named 'DrisBlueEighteen'".
Caster et al., U.S. Appl. No. 16/350,021, filed Sep. 13, 2018, titled "Blueberry Plant Variety Named 'DrisBlueSeventeen'".
Mowrey et al., U.S. Appl. No. 16/350,020, filed Sep. 13, 2018, titled "Blueberry Plant Variety Named 'DrisBlueSixteen'".

*Primary Examiner* — June Hwu
(74) *Attorney, Agent, or Firm* — Morrison & Foerster LLP

(57) ABSTRACT

A new and distinct variety of blueberry plant named 'DrisBlueNineteen', particularly selected as an early-season evergreen blueberry variety that needs no apparent chilling requirement to produce a large volume of high quality fruit, is disclosed.

9 Drawing Sheets

Latin name:
Botanical classification: *Vaccinium corymbosum* L.
Varietal denomination: The varietal denomination of the claimed variety of blueberry plant is 'DrisBlueNineteen'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueNineteen'.

Blueberry plant variety 'DrisBlueNineteen' was discovered in Hillsborough County, Fla. in April of 2011 and originated from a cross between the proprietary female parent blueberry plant 'DrisBlueSeven' (U.S. Plant Pat. No. 24,605) and the proprietary male parent blueberry plant '193C 4' (unpatented). The original seedling of the new variety was first asexually propagated via cuttings and tissue culture in Santa Cruz County, Calif. in May of 2011. 'DrisBlueNineteen' was subsequently asexually propagated via softwood cuttings and tissue culture from green shoots and underwent further testing in Santa Cruz County, Calif., Ventura County, Calif., and Hillsborough County, Fla. for five years (2013 to 2017). The present blueberry variety has been found to be stable and reproduce true to type through successive asexual propagations via softwood cuttings and tissue culture from shoot cuttings.

'DrisBlueNineteen' exhibits the following distinguishing characteristics when grown under normal horticultural practices in Santa Cruz County, Calif., Ventura County, Calif., and Hillsborough County, Fla.:

1. Strong plant vigor;
2. Early fruit maturation; and
3. Fruiting on one-year-old and current season's shoots.

'DrisBlueNineteen' was selected as an early-season evergreen blueberry variety that needs no apparent chilling requirement to produce a large volume of high quality fruit.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are four years old.

DETAILED BOTANICAL DESCRIPTION

Figure 1:
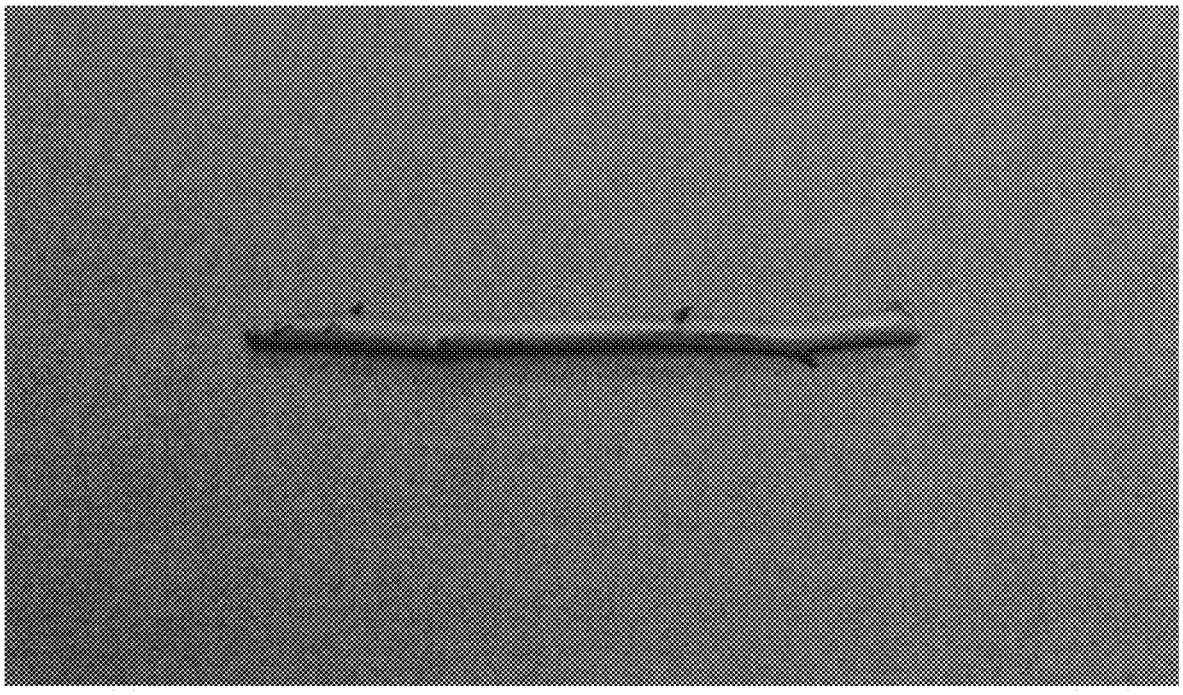
FIG. 1 illustrates a section of a current season one-year-old cane of variety 'DrisBlueNineteen'.
Figure 2:
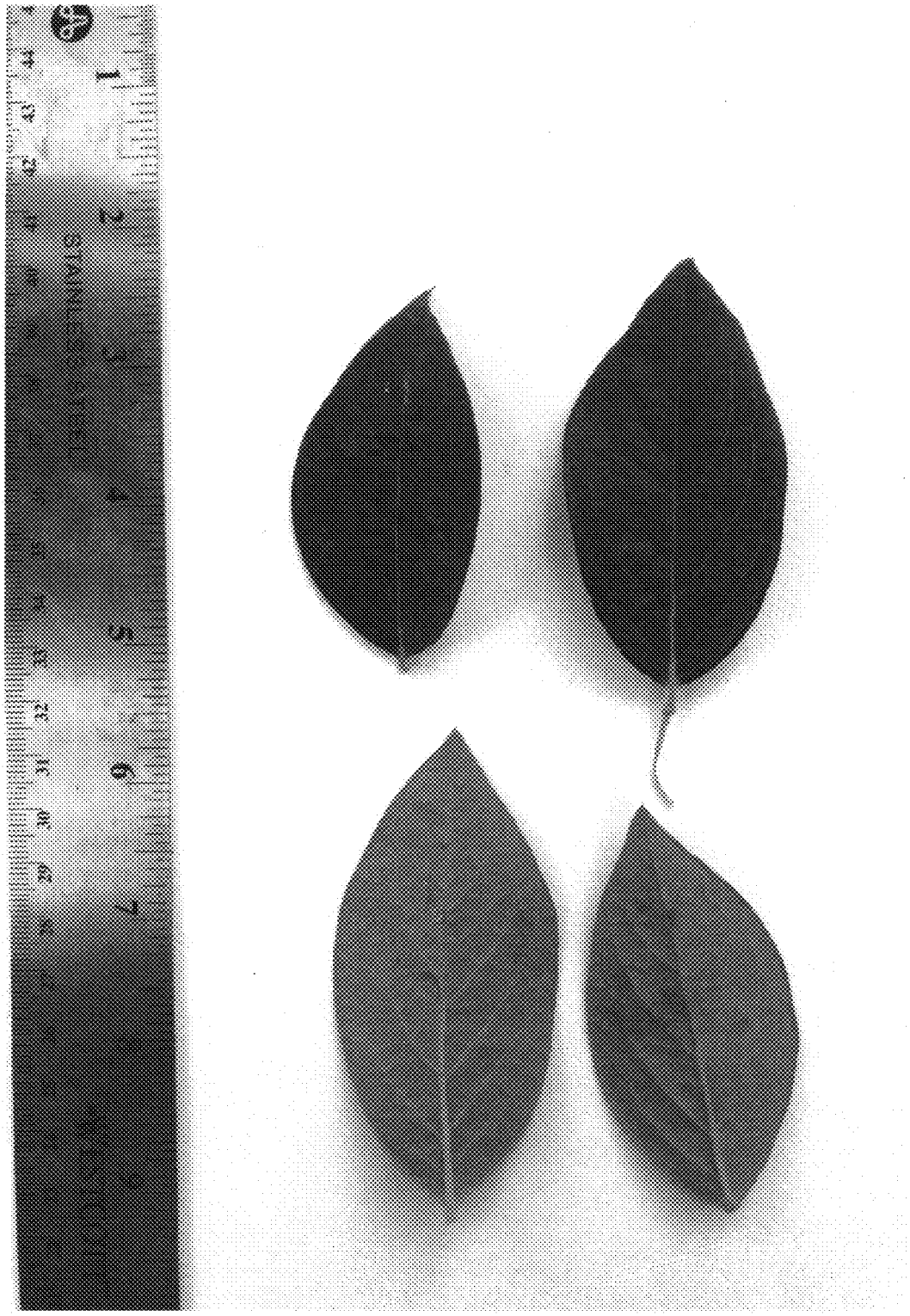
FIG. 2 illustrates leaves of variety 'DrisBlueNineteen'. The upper leaf surfaces are shown on the top and the lower leaf surfaces are shown on the bottom.
Figure 3:
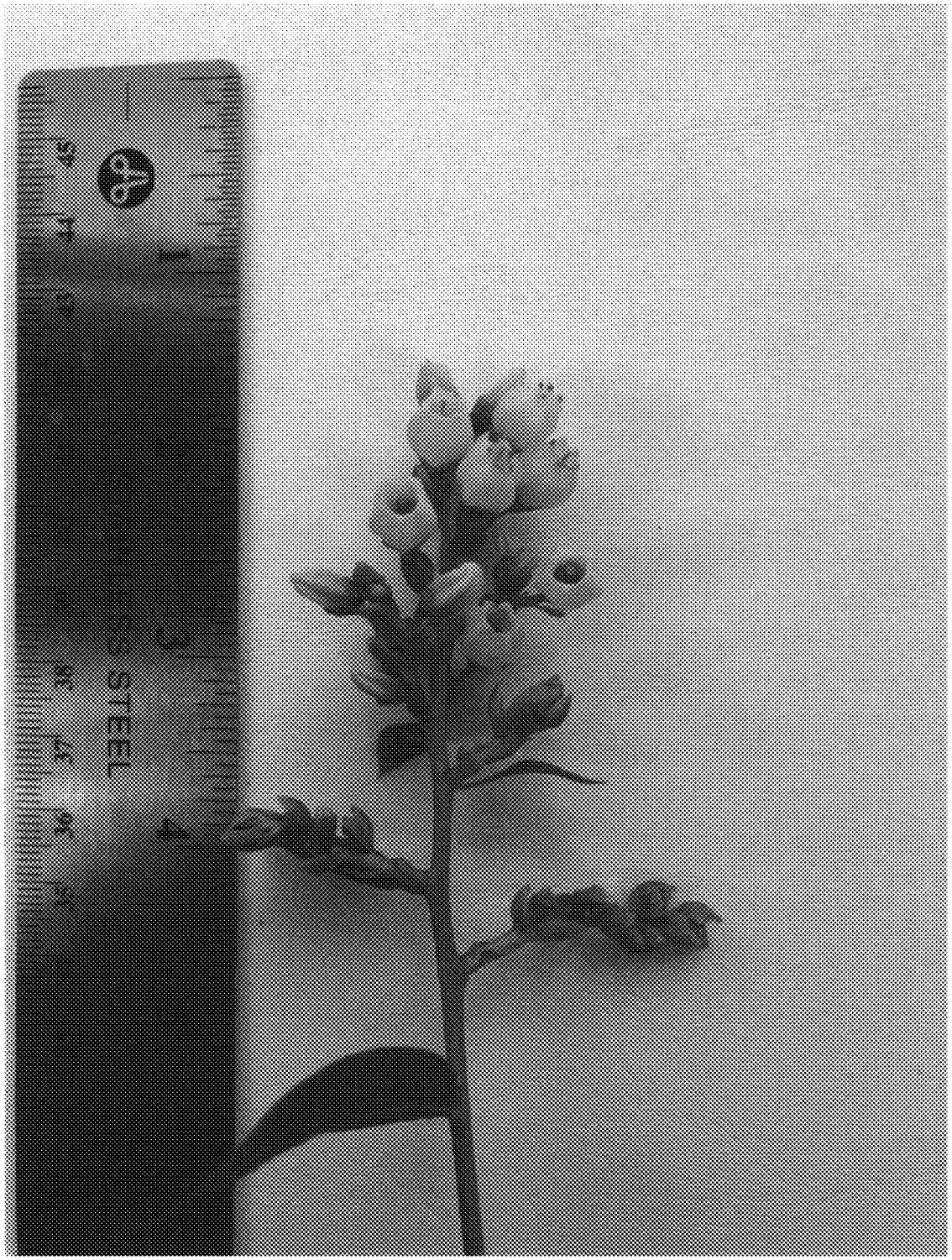
FIG. 3 illustrates a cluster of flowers and flower buds of variety 'DrisBlueNineteen'.
Figure 4:
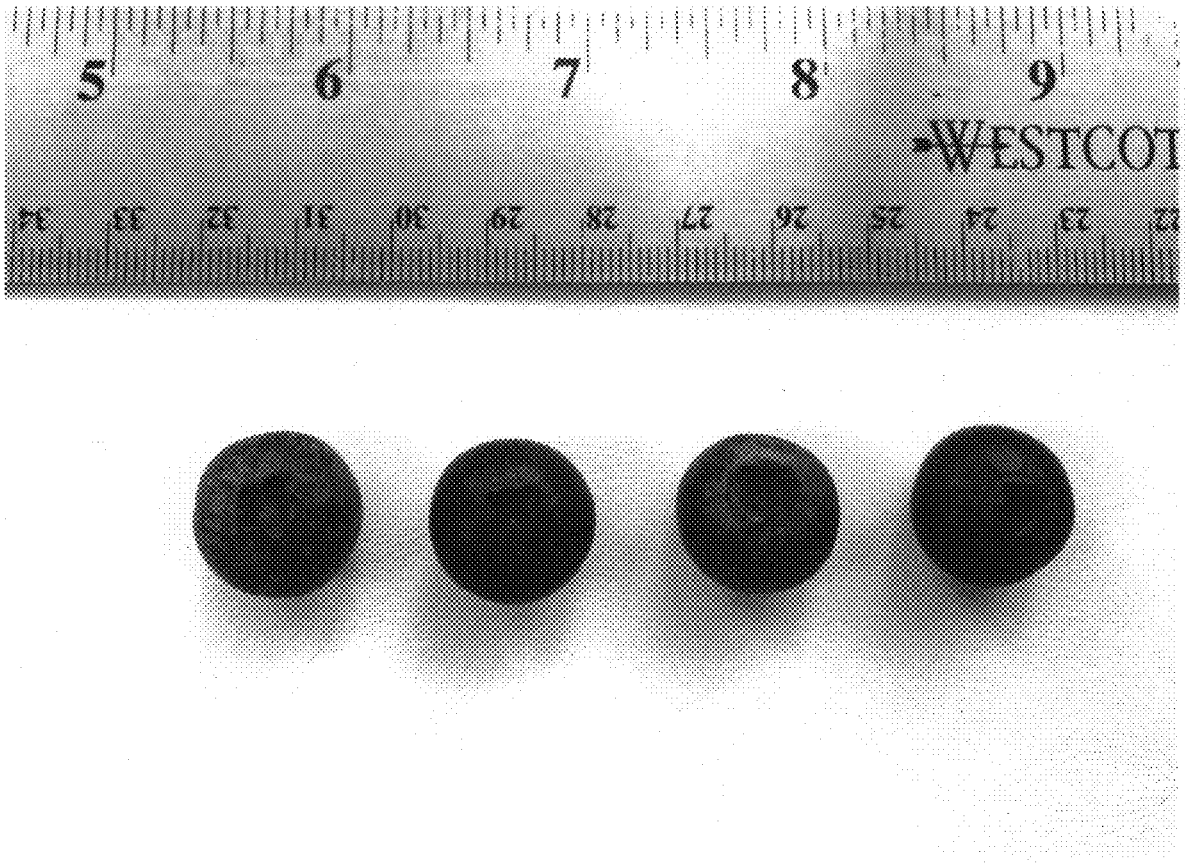
FIG. 4 illustrates a top (calyx basin) view of whole fruit of variety 'DrisBlueNineteen'.
Figure 5:
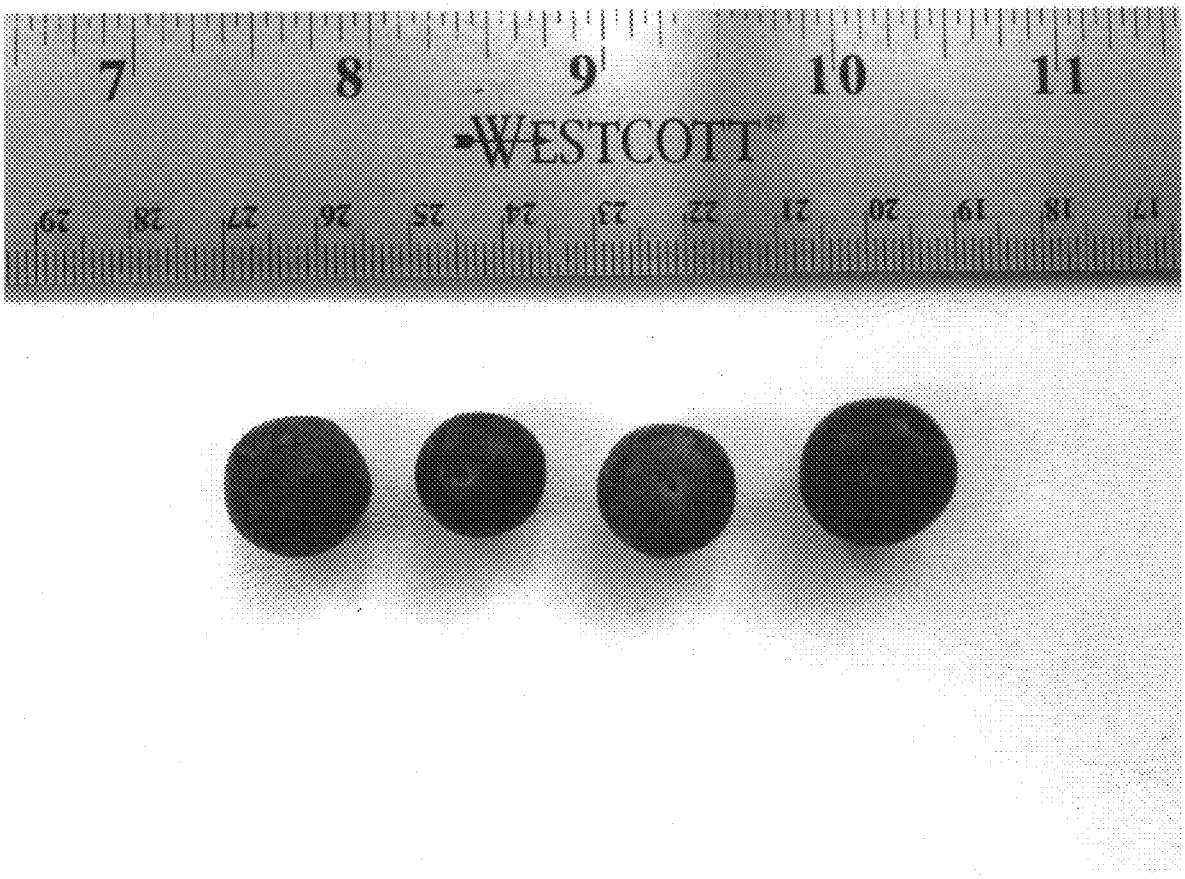
FIG. 5 illustrates a bottom (fruit-pedicel junction) view of whole fruit of variety 'DrisBlueNineteen'.
Figure 6:
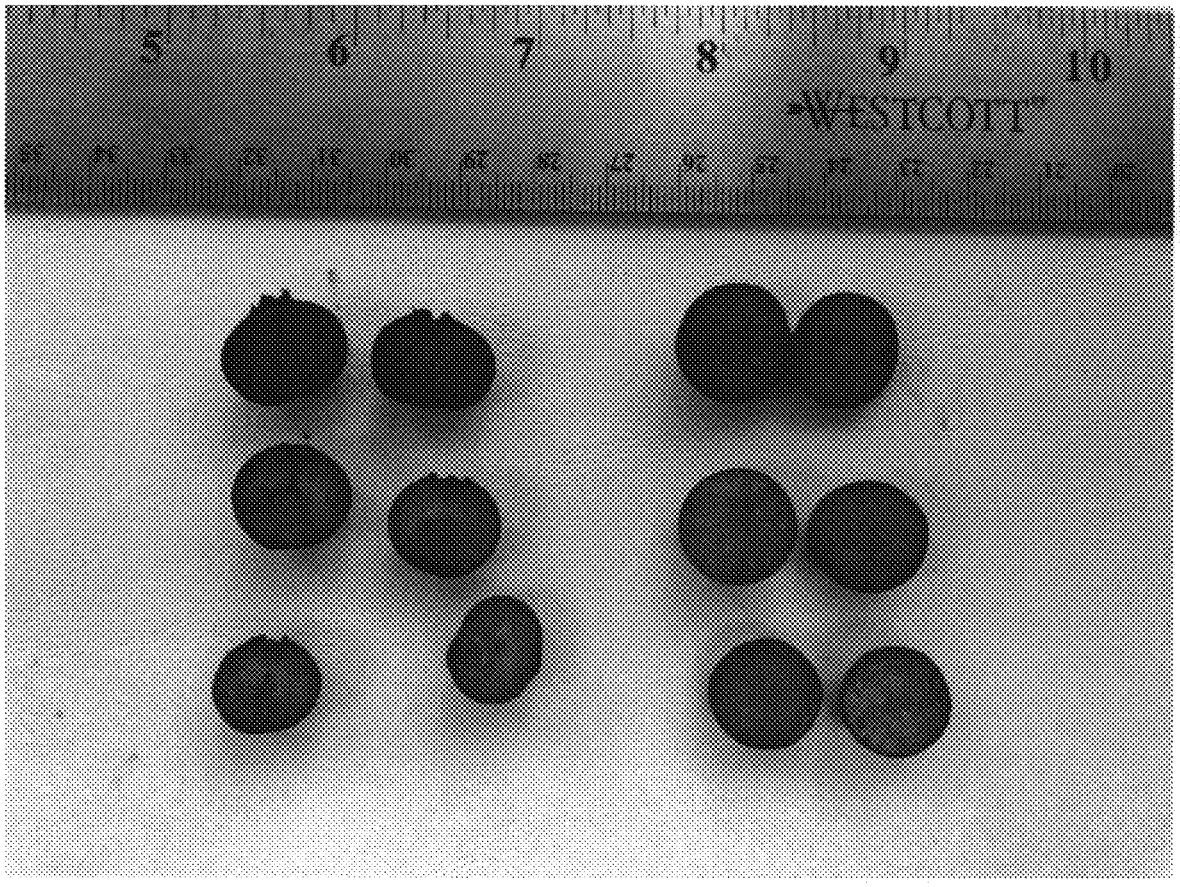
FIG. 6 illustrates cross-sections (right two columns) and longitudinal sections (left two columns) of the fruit of variety 'DrisBlueNineteen'.
Figure 7:
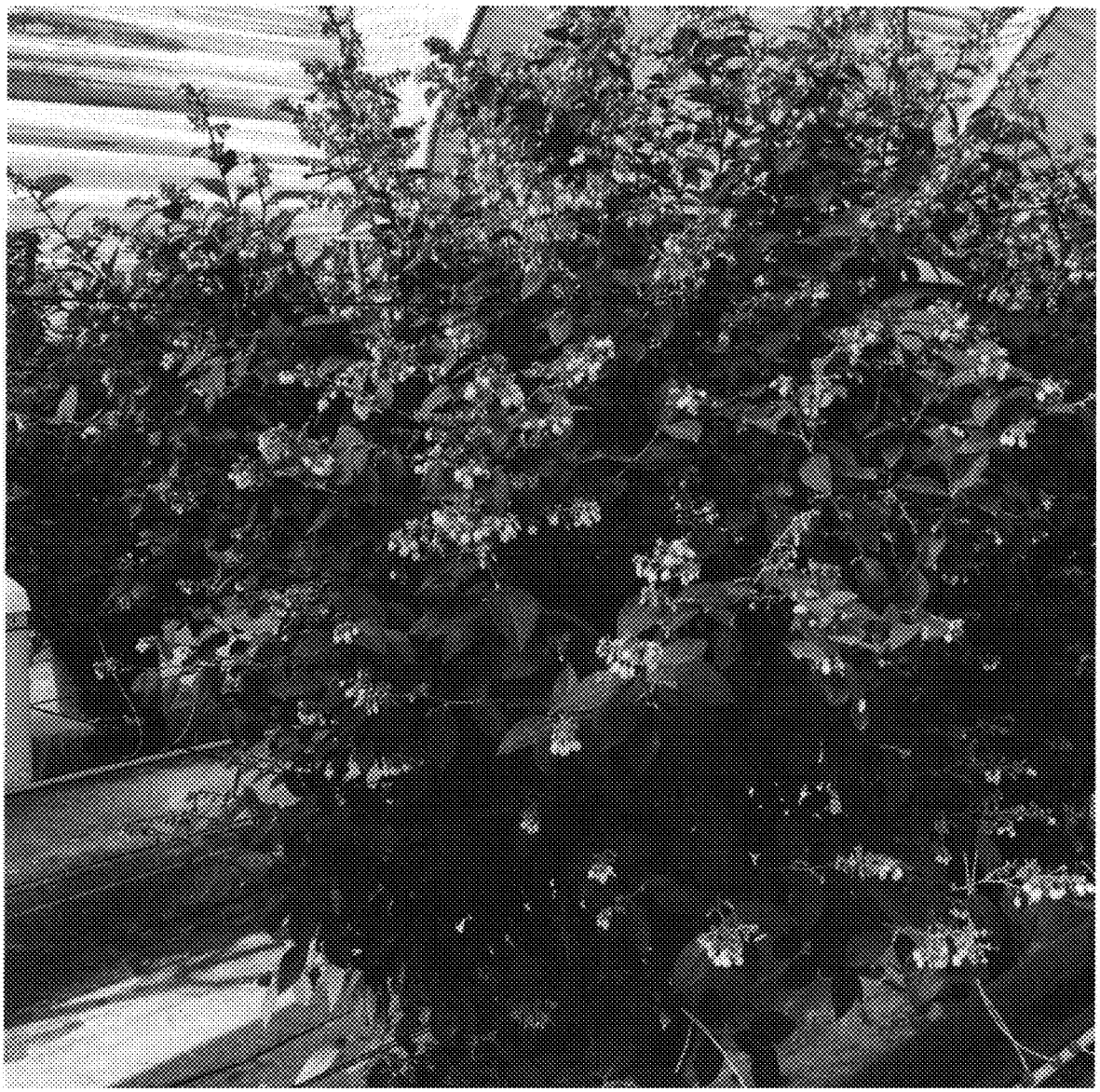
FIG. 7 illustrates plants bearing flowers of variety 'DrisBlueNineteen'.
Figure 8:
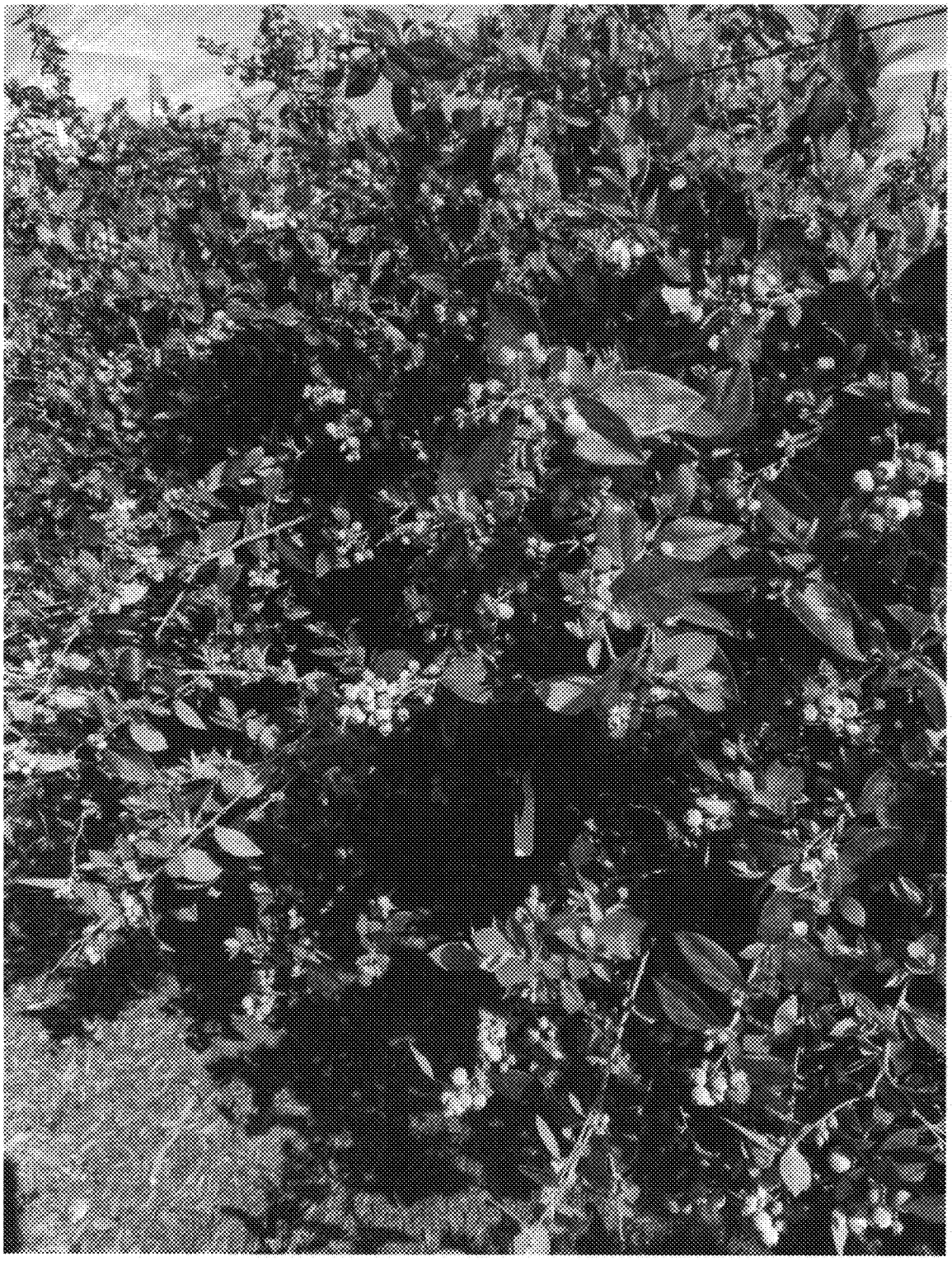
FIG. 8 illustrates plants bearing fruit of variety 'DrisBlueNineteen'.
Figure 9:
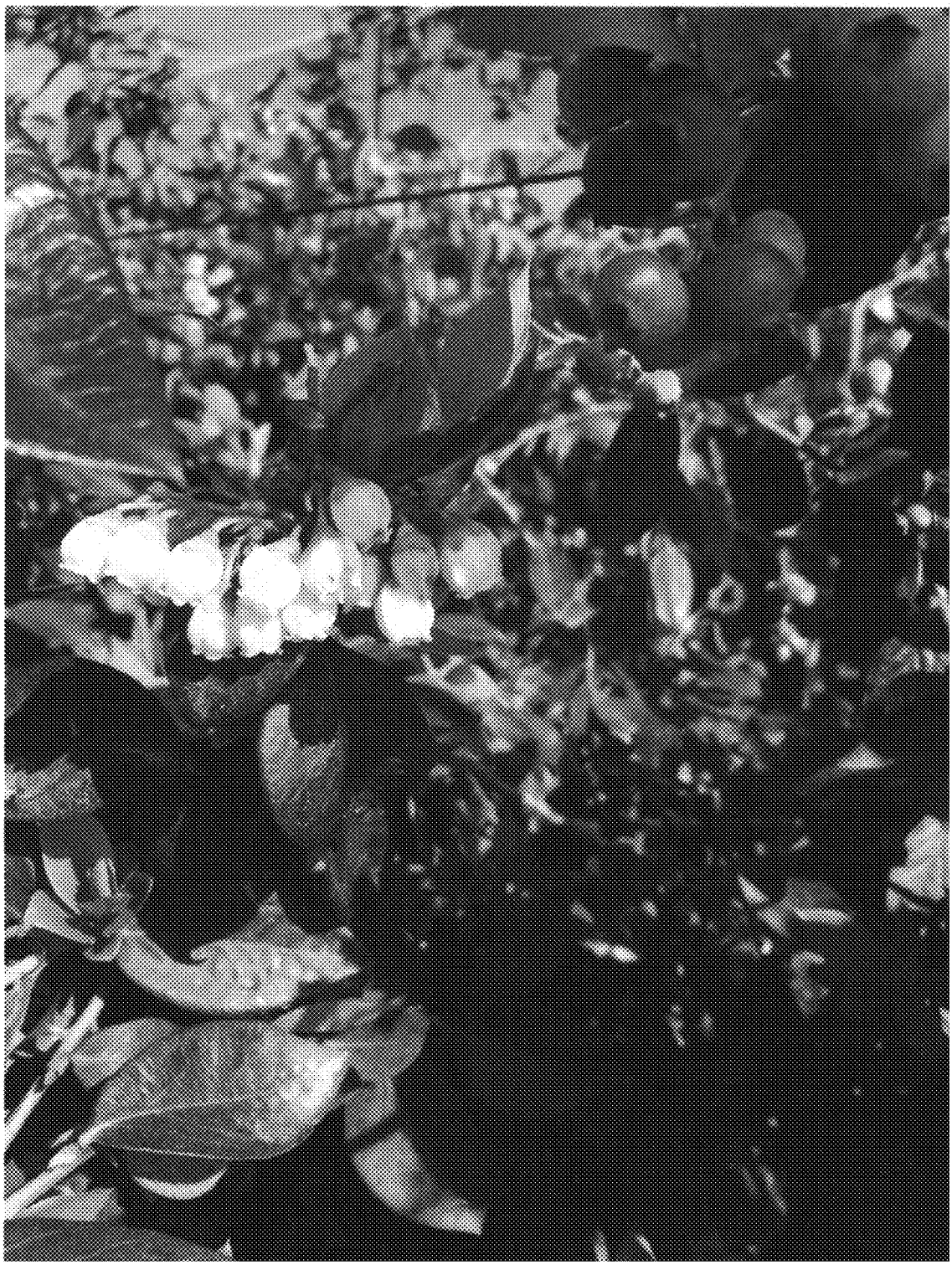
FIG. 9 illustrates plants bearing flowers and fruit of variety 'DrisBlueNineteen'.

The following description sets forth the distinctive characteristics of 'DrisBlueNineteen.' The data which define these characteristics is based on observations taken in Santa Cruz County, Calif., Ventura County, Calif., and Hillsborough County, Fla. from 2013 to 2017. This description is in accordance with UPOV terminology. Color designations, color descriptions, and other phenotypical descriptions may deviate from the stated values and descriptions depending upon variation in environmental, seasonal, climatic and cultural conditions. 'DrisBlueNineteen' has not been observed under all possible environmental conditions. The botanical description of 'DrisBlueNineteen' was taken from four-year-old plants, unless noted otherwise. The indicated values represent averages calculated from measurements of several plants. Color references are primarily to The R.H.S. Colour Chart of The Royal Horticultural Society of London (R.H.S.) (2007 edition), Descriptive terminology follows the *Plant Identification Terminology, An Illustrated Glossary,* $2^{nd}$ edition by James G. Harris and Melinda Woolf Harris, unless where otherwise defined.

Classification:

*Family.*—Ericaceae.
*Botanical.*—*Vaccinium corymbosum* L.
*Common name.*—Blueberry.
*Variety name.*—'DrisBlueNineteen'.

Parentage:

*Female parent.*—The proprietary blueberry plant 'DrisBlueSeven' (U.S. Plant Pat. No. 24,605).
*Male parent.*—The proprietary blueberry plant '193C 4' (unpatented).

Plant:

*Height.*—138.17 cm.
*Width.*—182.3 cm.
*Length/width ratio.*—0.8.
*Growth habit.*—Semi-upright.
*Internode length.*—15.49 mm.
*One-year-old canes* (*young canes*).—Length: 55 cm. Diameter at the base: 9 mm. Diameter at the tip: 8 mm. Internode length on the upper half: 3.7 cm. Color: RHS 146B (Moderate yellow-green).
*Five-year-old canes* (*mature canes*).—Length: 40 cm. Diameter at the base: 31 mm. Diameter at the tip: 19 mm. Five-year-old cane surface texture: Rough. Five-year-old cane color: RHS 199B (Light olive brown).

Leaves:

*Length.*—80.6 mm.
*Width.*—40.3 mm.
*Length/width ratio.*—2.0.
*Shape.*—Ovate.
*Margin.*—Entire.
*Color on upper side.*—RHS N189 (Greyed green).
*Color of lower side.*—RHS 191A (Greyish yellow-green).
*Shape of the leaf apex.*—Cuspidate.
*Shape of the leaf base.*—Cuneate.
*Petiole.*—Length: 3.1 mm. Diameter: 1.30 mm. Petiole color: RHS 144D (Light yellow-green).

Flowers:

*Inflorescence length*.—Medium.

*Length of flower* (*excluding peduncle*).—9.55 mm.

*Diameter of flower*.—7.78 mm.

*Length/width ratio*.—1.2.

*Flower bud*.—Length: 10.54 mm. Width: 3.69 mm. Number of flowers per bud: 8. Flower bud anthocyanin color: RHS 31A (Orange-red).

*Pedicel*.—Length: 6.27 mm. Diameter: 0.99 mm.

*Corolla*.—Shape: Urceolate. Anthocyanin coloration of corolla tube: Absent. Ridges on corolla tube: Present. Petal width (ridge to ridge): 4.12 mm. Diameter of corolla aperture: 3.36 mm. Corolla color: RHS NN155B (White).

*Reproductive organs*.—Style length (including stigma): 7.83 mm. Style color: RHS 141D (Strong yellow-green). Ovary color: RHS 141A (Deep yellowish green). Anther color: RHS N167A (Brownish orange).

*Flowering interval on one-year shoot*.—January to May.

*Flowering interval on current season's shoot*.—November to January.

*Pollinator requirement*.—Insect pollinators such as honeybees or bumblebees are recommended.

Fruit:

*Length*.—13.02 mm.

*Diameter*.—15.87 mm.

*Length/width ratio*.—0.8.

*Shape in longitudinal section*.—Round.

*Attitude of sepals*.—Semi-erect.

*Type of sepals*.—Straight.

*Calyx basin*.—Diameter: 6.14 mm. Depth: 3.48 mm. Diameter/depth ratio: 1.8.

*Weight*.—2.1 g.

*Number of berries per cluster*.—8.

*Peduncle* (*stalk of a fruit cluster*) *length*.—101.67 mm.

*Diameter of pedicel* (*stalk of a single fruit*).—1.08 mm.

*Seed*.—Length: 1.77 mm. Width: 0.82 mm. Length/width ratio: 2.2.

*Color of unripe fruit*.—RHS 138C (Moderate yellow-green).

*Color of fruit skin* (*with bloom*).—RHS 102B (Moderate blue).

*Color of fruit skin* (*after removal of bloom*).—RHS 103A (Greyish purplish blue).

*Intensity of fruit bloom*.—Medium.

*Color of fruit flesh*.—RHS 146C (Moderate yellow-green).

*Fruit firmness*.—Firm.

*Fruit acidity*.—Low.

*Fruit sweetness*.—Medium.

*Fruiting type*.—On one-year-old and current season's shoots.

*Ripening interval on one-year-old shoot*.—January to May.

*Ripening interval on current season's shoot*.—November to January.

*Market use of fruit*.—Fresh market.

*Fruit storage life*.—Following harvest, fruit have been stored for 21 days when maintained under cooled temperatures that are standard for blueberry storage.

*Yield*.—4.5 kg/plant to 5.5 kg/plant of fruit per season from 48-month-old plants when grown in Ventura County, Calif.

Resistance to abiotic stress, pests, and diseases:

*Drought*.—Susceptible.

*Heat*.—Moderately resistant.

*Blueberry bud mite* (*Acalitus vaccinii*).—Moderately susceptible.

*Aphids*.—Moderately susceptible.

*Botryosphaeria stem blight*.—Susceptible.

COMPARISONS TO PARENTAL AND COMMERCIAL BLUEBERRY VARIETIES

'DrisBlueNineteen' differs from the proprietary female parent and commercial blueberry plant variety 'DrisBlueSeven' (U.S. Plant Pat. No. 24,605) in that fruit of 'DrisBlueNineteen' mature earlier and have a lighter blue color compared to fruit of 'DrisBlueSeven'. Further, plants of 'DrisBlueNineteen' have a more upright growth habit and are more vigorous than plants of 'DrisBlueSeven'. Additionally, 'DrisBlueNineteen' has a fruiting type of fruiting on one-year-old and current season's shoots, whereas 'DrisBlueSeven' has a fruiting type of fruiting on one-year-old shoots.

'DrisBlueNineteen' differs from the proprietary male parent '193C 4' (unpatented) in that 'DrisBlueNineteen' has higher consistent yield and produces firmer fruit when compared to '193C 4'.

'DrisBlueNineteen' differs from the commercial blueberry plant variety 'Biloxi' (unpatented) in that 'DrisBlueNineteen' has a more upright plant habit, larger and more uniform berry size, and improved post-harvest performance when compared to 'Biloxi'.

What is claimed is:

1. A new and distinct variety of blueberry plant designated 'DrisBlueNineteen' as shown and described herein.

* * * * *